United States Patent [19]

Bordovsky et al.

[11] Patent Number: 4,709,712
[45] Date of Patent: Dec. 1, 1987

[54] POLYCARBOXYLIC ACID POLYMER GELS AS PROTECTIVE AGENTS

[75] Inventors: Michael J. Bordovsky; John W. Feik, both of San Antonio, Tex.

[73] Assignee: Dermatalogical Products of Texas, Fort Worth, Tex.

[21] Appl. No.: 921,496

[22] Filed: Oct. 22, 1986

[51] Int. Cl.$^4$ .............................................. A45D 7/00
[52] U.S. Cl. ........................................................ 132/7
[58] Field of Search ................................ 132/7; 424/70

[56] References Cited

U.S. PATENT DOCUMENTS 4,551,330 11/1985 Wagman ................................. 132/7
4,592,908 6/1986 Wajaroff ................................ 132/7
4,660,580 4/1987 Hoch ....................................... 132/7

Primary Examiner—Gregory E. McNeill
Attorney, Agent, or Firm—James A. Arno; Gregg C. Brown

[57] ABSTRACT

Disclosed are aqueous gel compositions comprising a polycarboxylic acid polymer and, optionally, a dermatologically safe buffering system to maintain a pH in the range 4.5 to 7.0; also disclosed are methods of treatment comprising topically applying said gel compositions to selected locations on the scalp to protect the host subject from caustic run-off during hair treatment with, for example, permanent wave solutions.

8 Claims, No Drawings

POLYCARBOXYLIC ACID POLYMER GELS AS PROTECTIVE AGENTS

BACKGROUND OF INVENTION

This invention relates to a product and means for protecting the scalp during hair treatment procedures which involve the use of caustic solutions, such as those used in hair straightening or hair waving operations. Specifically, this invention relates to the use of polymers having acidic functional groups, such as, polycarboxylic acid polymers, which readily form acidic aqueous gels, per se, and which are amenable to the inclusion of dermatologically safe buffering systems to achieve enhanced capacity in the pH range 3.5 to 7.0.

One of the most common hair treatments involves inducing a curl or wave by contacting the hair with solutions which are inherently irritating to the scalp and, via runoff, to the neck and shoulders because of the alkaline nature of the solution employed. Hair straightening procedures are similarly subject to this observation. Prior attempts to make the host subject comfortable during such hair treatments included the use of barrier creams such as petroleum jelly or the use of cotton dams placed at strategic positions against the scalp. Such prior attempts, however, have enjoyed limited and not always reproducible success.

DETAILED DESCRIPTION OF THE INVENTION

The present invention, in its product aspect, comprises aqueous gels of acidic polymers, such as polycarboxylic acid polymers, which can be used, in the method aspect of the present invention, alone or in combination with a dermatologically safe and comfortable buffering system to provide an enhanced buffering capacity within the pH range of 3.5 to 7.0.

Suitable polymers useful in the present invention are carboxylvinyl polymers. Preferred polymers of this class include the so called Carbomers, available under the trade name Carbopol from the B.F. Goodrich Company; and ethylene maleic anhydride polymeric materials available under the tradename EMA from the Monsanto Company. The known and readily available polymers Carbopol 934 and 940 are specifically preferred. The polymers are used in the aqueous gel compositions of the present invention in the range from 2% to 4% weight percent.

Polysulfonic acid polymers which are capable of forming aqueous gels are also suitable, for example, certain polyacrylamidomethylpropane sulfonic acids. Such polymers are known; see for example U.S. Pat. No. 3,128,631, which is incorporated herein by reference to the extent that it defines such polymers and how to make them. A representative example of such polysulfonic acids, known as Cosmedia Polymer HSP-1180, is available commercially from Henkel Chemicals.

The most preferred polycarboxylic acid polymer of the present invention is Carbomer 940 either per se or incorporated with a buffering system to enhance the capacity to resist change of pH from the desired range of 4.5 to 7.0. Buffering systems employing acid such as acetic, citrate or phosphoric and their salts are preferred. The use of buffers, however, improves capacity against pH change and give a greater margin of safety and comfort. An especially preferred buffering system comprises sodium acetate and acetic acid to achieve a pH of 4.5 to 7.0. For cosmetic appeal, the finished product may be colored and it may additionally contain pleasing sensory agents, such as menthol. However, with respect to pH, it should be noted that Carbomer 940 in a 3.0 wt. % gel has a generally adequate capacity to maintain the pH in the desired pH 4.5-7.0 without the use of buffers, provided that the gel state is achieved by disolution of the polymer with initial adjustment of the pH by a base, such as, ethanolamine, or the like.

In practice of the present invention, prior to treating the hair with the caustic permanent wave solution or the like, a barrier, in the form of the buffered carbomer gel, is applied at selected locations on the scalp, neck and forehead and may be left as such or there may be additionally employed cotton strips or cotton batting to absorb the caustic solution prior to its neutralization; wherein said cotton or equivalent absorbent material is secured to the subject by the pattern of gel material first applied.

The following example is representative of the formulation.

FORMULA (Wt. %)

Carbomer 940: 3.0
Triethanolamine: 2.0
Sodium Acetate: 1.0
Acetic Acid: 0.05
Germaben II: 0.8
Glycerin: 2.5
FD&C Blue #1: 0.0001
Purified Water: qs The above formulation is prepared in the following way:

Approximately 80% of the available water phase is weighed into an appropriately sized round bottom kettle. Use of a kettle is necessary to obtain adequate product mixing and reduces likelihood of "dead spots" during the mixing process. The water soluble ingredients are added in the following order: Germaben II, acidic acid (glacial) and then glycerin.

The mixture is stirred continuously during the addition of the water soluble ingredients to insure uniform dissolution. The solution is then mixed for a minimum of ten minutes.

A high sheer mixer with variable rpm, height adjustments and blade sizes are required to obtain proper stirring patterns for hydration of the carbomer mixture.

The mixer rpm, height and blade size is adjusted so that a vortex is obtained while stirring the water phase. The carbomer 940 is slowly sprinkled into the middle of the vortex. Caution must be exercised to prevent formation of lumps while the carbomer is being added to the water phase. The mixture is stirred for approximately 80 to 90 minutes to achieve full hydration and homogeneity.

The hydrated carbomer mixture is removed from the high sheer mixer and the kettle placed under a mixer which provides counter motion mixing and side scraping. A solution of the colorant in a portion of the available water is added to the carbomer mixture while mixing.

A separate solution of triethanolamine using a portion of the available water is prepared. (Note: This solution serves to solubilize the carbomer dispersion to obtain product clarity and proper pH). After addition of the triethanolamine solution, the product is stirred to obtain uniform reaction with the carbomer phase.

A separate solution of sodium acetate (trihydrate) is prepared. When the sodium acetate is completely dissolved, it is then added to the partially neutralized carbomer phase and mixed for 90 minutes to obtain complete uniformity.

Relative to the example above, it is understood that the Carbomer 940 may be present at a weight percent of from 2% to 4%, that the triethanolamine base is representative of any dermatologically safe base which is employed to solubilize the Carbomer 940 and adjust the pH to the desired range of 4.5 to 5.5.

What is claimed is:

1. A method of protecting the scalp during hair treatment procedures involving the use of caustic solutions comprising first contacting exposed scalp with an aqueous gel of an acidic polymer gel having a pH of 4.5 to 5.5.

2. A method according to claim 1 wherein the polymer is a carboxyvinyl polymer.

3. A method according to claim 2 wherein the polymer is Carbomer 940 present at a concentration of from 2.0 to 4.0% by weight.

4. A method according to claims 1, 2 or 3 wherein absorbent dams are secured at locations on the scalp defined by the pattern of the first/applied gel material.

5. A hair treatment composition comprising an acidic polymer at a 2.0-4.0% by weight in the form of an aqueous gel having a pH of 4.5 to 5.5.

6. A gel, according to claim 3 wherein acidic polymer is Carbomer 940 and is present in an amount of 2% to 4%.

7. A hair treatment aqueous gel composition comprising 2.0 to 4.0% wt. % of a carboxyvinyl polymer and a dermatologically safe buffering system to maintain the pH at 4.5 to 7.0.

8. The composition of claim 7, wherein the polymer is Carbomer 940 and the buffer system comprises sodium acetate - acetic acid.

* * * * *